United States Patent [19]

Blum et al.

[11] Patent Number: 5,017,529

[45] Date of Patent: * May 21, 1991

[54] PROCESS FOR MAKING CERAMIC MATERIALS

[75] Inventors: Yigal D. Blum, Menlo Park; Richard M. Laine, Palo Alto, both of Calif.

[73] Assignee: SRI International, Menlo Park, Calif.

[*] Notice: The portion of the term of this patent subsequent to Jan. 31, 2006 has been disclaimed.

[21] Appl. No.: 449,495

[22] Filed: Dec. 1, 1989

Related U.S. Application Data

[60] Continuation of Ser. No. 251,560, Sep. 30, 1988, abandoned, which is a division of Ser. No. 907,395, Sep. 15, 1986, Pat. No. 4,801,439.

[51] Int. Cl.$^5$ .................. C04B 35/58; C04B 35/56
[52] U.S. Cl. .................................. 501/95; 501/96; 501/98
[58] Field of Search ................. 501/96, 98, 95

[56] References Cited

U.S. PATENT DOCUMENTS

| | | |
|---|---|---|
| 2,809,171 | 10/1957 | Hough et al. |
| 3,711,594 | 1/1973 | Bienert et al. .............. 501/96 X |
| 4,495,123 | 1/1985 | Hunold et al. .............. 501/96 X |
| 4,545,968 | 10/1985 | Hirano et al. .............. 501/96 X |
| 4,562,163 | 12/1985 | Endo et al. .............. 501/96 |
| 4,581,468 | 4/1986 | Paciorek et al. .............. 501/96 X |
| 4,707,556 | 11/1987 | Paciorek et al. .............. 501/96 X |
| 4,749,556 | 6/1988 | Parrish et al. .............. 501/96 X |
| 4,767,728 | 8/1988 | Riccitiello et al. .............. 501/91 |
| 4,784,978 | 11/1988 | Ogasawara et al. .............. 501/96 |
| 4,801,439 | 1/1989 | Blum et al. .............. 423/284 |

FOREIGN PATENT DOCUMENTS 51-53000  5/1976  Japan .

OTHER PUBLICATIONS

Laubengayer et. al., (1961), *J. Am. Chem. Soc.*, 83:1337–1342.
Hawthorne, (1959), *J. Am. Chem. Soc.*, 81:5836–5837.
Hawthorne, (1961), *J. Am. Chem. Soc.*, 83:833–834.
Aubrey et al., (1959), *J. Chem. Soc.*, pp. 2927–2931.
Mellon et al., (1963), *Adv. Inorg. Chem. and Radiochem.*, 5:259–305.
Burch et al., (1962), *J. Chem. Soc.*, pp. 2200–2203.
Narula et al., in "Better Ceramics Through Chemistry", Symposium, *Mat. Res. Soc.*, (1986).
Bender et al., (1985), *Ceram. Eng. Sci. Proc.*: 6(7–8):11-71–1183.
Komm et al., (1983), *Inorganic Chem.*, 22(11):1684–1686.
Narula et al., (1987), *J. Am. Chem. Soc.*, 109:5556–5557.
Paciorek et al., (1986), *J. Polymer Sci.*, 24:173–185.

*Primary Examiner*—Karl Group
*Attorney, Agent, or Firm*—Dianne E. Reed

[57] ABSTRACT

A process for preparing tractable preceramic precursors of Group IIIA metal/Group VA nonmetal compounds, such as BN, in which a first reactant containing a Group VA nonmetal to hydrogen bond, such as ammonia or an amine is reacted with a second reactant containing a Group IIIA metal to hydrogen bond, such as a metal hydride, in the presence of a metal catalyst that catalyzes dehydrocoupling of the bonds to form the precursor. Further reaction of the precursor in the presence of the catalyst forms oligomeric/polymeric forms of the precursor.

19 Claims, No Drawings

PROCESS FOR MAKING CERAMIC MATERIALS

This application is a continuation of application Ser. No. 07/251,560, filed Sept. 30, 1988 now abandoned which is a division of Ser. No. 06/907,395 filed Sept. 15, 1986 which is now U.S. Pat. No. 4,801,439.

DESCRIPTION

1. Technical Field

This invention is in the field of organometallic chemistry. More particularly, it concerns the catalytic synthesis of compounds that contain a non-Lewis acid/base bond that are precursors to Group IIIA metal-Group VA nonmetal compounds and ceramic materials, such as boron nitride.

2. Background

Boron nitride (BN) is commercially available and is relatively inexpensive as a powder. Practical applications of BN, however, require that the BN be in the form of a coating, fiber or monolith rather than as a powder. Although coatings can be derived from the powder by physical vapor deposition, processes for converting BN powder into fibers are not available currently and processes for transforming powder into monoliths are energy and equipment intensive. Accordingly, there is a need to provide an effective manner of providing BN in forms other than as a powder.

A possible way of doing this is to use tractable "preceramic" BN precursors that can be manipulated into the desired form and then pyrolyzed to BN. Polymeric amine/boron compounds such as polyaminoboranes (PABs) and polyborazines (PBZs), representative structures of which are set forth below, are potential precursors to BN.

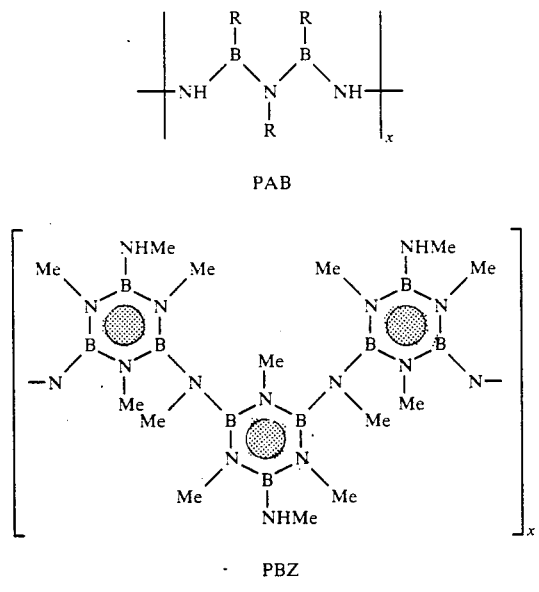

Me = methyl, x represents a positive integer

In fact, PABs and PBZs have been shown to give BN on pyrolysis (Inorg. Chem. (1963) 2:29). There is not presently available, however, a selective, high yield synthetic route for making nonvolatile, but tractable PABs and PBZs that can be converted to high yield ceramics.

In current low temperature amine/borane chemistry Lewis acid-Lewis base interactions dominate almost all of the known reaction chemistry of amines with boranes. The strength of the Lewis acid-Lewis base bond drives aminoboranes to form volatile tricyclomeric complexes or intractable polymers. Low temperature amine/borane chemistry that involves such interactions usually do not provide a feasible synthetic route to tractable oligomeric or polymeric BN precursors.

Other synthetic routes that are currently available to produce tractable PABs and PBZs rely on heating the reactants to high temperatures to obtain condensation-like products Heating the aminoborane complex $NH_3 \cdot BH_3$ to its decomposition point, for instance, provides mixtures of condensed oligoborazines with limited solubilities in common organic solvents. If this reaction is run above 200° C. both borazine and insoluble condensed PBZs are produced (Laubengayer, A. W., et al. J Am Chem Soc (1961) 83:1337). On heating, these insoluble PBZs decompose at 900° C. to give moderate yields of BN. Similar reactions using substituted aminoboranes, lower temperatures and ammonium chloride as a catalyst yield substituted borazine and oligomeric compounds (Hawthorne, J., J Am Chem Soc (1959) 81:5836 and J Am Chem Soc (1961) 83:833). When borazine is heated to temperatures of 340° C. to 380° C. it rearranges to form higher aromatic-like compounds (Laubengayer. A. W., et al. supra). These condensed aromatic-like compounds can be converted to BN by pyrolysis; unfortunately, however, many of them are intractable solids or too volatile which makes them unattractive as preceramic materials.

Two alternative approaches to the synthesis of PABs and PBZs derive from the condensation reactions of trisaminoboranes (Aubrey. D. W. and Lappert. M. F., J Chem Soc (1959) 2927: and Burch, J. E., et al. J Chem Soc (1962) 2200). These reactions provide soluble cross-linked elastomers; but, the reaction temperatures are again quite high and this significantly affects yields and selectivities.

U.S. Pat. No. 2,809,171 discloses that linear PABs are produced by heating isopropylaminoborane at 300° C. This approach to tractable PABs works but the presence of the relatively large isopropyl group will lead to low ceramic yields. Also, as indicated, the synthesis requires relatively high reaction temperatures.

There are three reports that describe the synthesis of tractable PBZs used as ceramic precursors. Japanese Kokai patent publication 76/53,000 (1976) describes the preparation of preceramic PBZs by the following reaction:

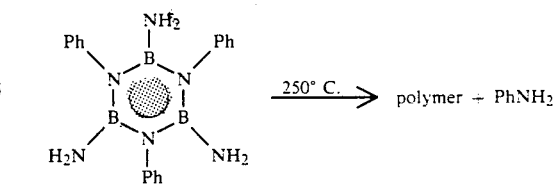

Ph = phenyl

The polymer produced by this reaction was successfully converted into a preceramic fiber and thence to a BN fiber by pyrolysis. Again, however, this synthesis requires high temperatures and most likely suffers from lack of selectivity and low ceramic yields.

The second report (Narula, C. K., et al, "Better Ceramics Through Chemistry" Symposium, Mat Res Soc (1986) in press) describes the preparation of methyl-substituted PBZs at low temperatures by the following scheme:

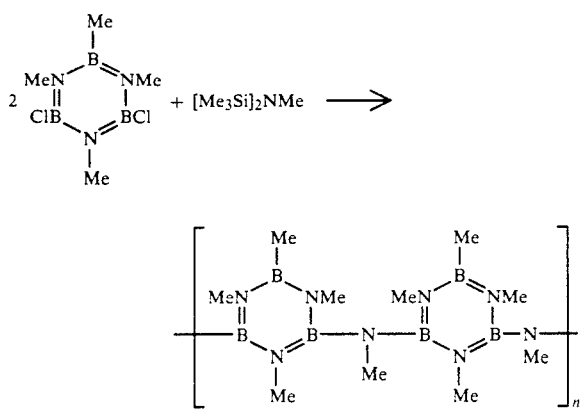

Pyrolysis of these polymers provides ceramic yields of <50%. The ceramic products are not completely characterized but are low in nitrogen and contain some silicon. Some of the reported problems using this approach include difficulties with solvent removal at low temperatures, incomplete reaction of all the substituents as evidenced by the evolution of ammonium chloride during pyrolysis and the fact that the precursors are usually gels that are not suitable for spinning.

The third report involves unpublished attempts to synthesize PBZs using silicon chloride elimination reactions of the following type:

$(Me_3SiNH)_2BCl \rightarrow Me_3SiCl + [(Me_3SiNH)BNH]_3 \rightarrow [(Me_3SiNH)BNH]_x$ While these polymers do produce BN upon pyrolysis the ceramic yields are on the order of 20%-30% because the trimethylsilyl ligands must be lost in the conversion process.

Summarizing the current state of the art relating to synthesizing BN preceramic polymers leads to the following conclusions:

1. The low-temperature chemistry of aminoboranes is dominated by their Lewis acid-Lewis base interactions which limits synthetic routes to tractable polymers.

2. Those synthetic routes that are available require relatively high temperatures which leads to poor selectivity and low overall yields of tractable precursors.

3. Tractable BN preceramic polymers currently available contain high weight percents of extraneous side groups (e.g. isopropyl and phenyl groups) that lead to low ceramic yields.

A primary object of the present invention is to provide a novel low temperature catalytic synthesis of BN precursors, precursors to compounds of boron/other Group VA nonmetals, and precursors for other Group IIIA metal/Group VA nonmetal compounds.

In addition to being preceramic materials, compounds containing B—N bonds may be useful as synthetic reagents. For example, tris(dimethylamino)borane is a useful reagent for boron templated cyclization in total synthesis of monocyclic spermidine alkaloids. Group IIIA metal-Group VA nonmetal ceramics other than BN have various commercial applications. For instance, AlN is a high refractory and chemical resistant with important physical and electronic properties and GaAs offers semiconductor properties not available with Si-based electronic materials.

DISCLOSURE OF THE INVENTION

The invention is a process for producing a compound containing at least one non-Lewis acid/base Group IIIA metal-Group VA nonmetal bond comprising reacting a first reactant that has a Z—H bond where Z represents a Group VA nonmetal and a second reactant that has an M—H bond where M is a Group IIIA metal in the presence of a metal catalyst that catalyzes dehydrocoupling of the Z—H and M—H bonds, whereby said compound is formed.

When the process is used to make compounds having a multiplicity of M—Z bonds the metal component of the bonds may be the same or different and the nonmetal component of the bond may be the same or different.

When this synthesis scheme is used to prepare BN precursors, Z represents nitrogen and M represents boron.

Also included within the invention is a process comprising cleaving the M—Z bond of an M—Z bond-containing compound prepared as above or otherwise using a metal catalyst that activates the bond in the presence or absence of hydrogen or a hydrogen donor, and reacting the cleavage product to produce an M—Z bond-containing compound. Oligomeric or polymeric compounds containing a multiplicity of M—Z bonds may be made by this process.

The invention also includes certain novel preceramic and ceramic products.

The novel preceramics are compositions prepared by reacting an amine borane complex with a polysilazane in the absence or in the presence of a metal catalyst that catalyzes dehydrocoupling of B—H and N—H bonds. Preferably the polysilazane is of the formula $(H_2SiNMe)_x$ where Me represents methyl and x represents an integer greater than 4. Novel ceramic products are made by pyrolyzing the above preceramic.

Another group of novel ceramics are the products prepared by (a) reacting $BH_3 \cdot NMe_3$, where Me represents methyl with methylamine in the presence of a metal catalyst that catalyzes dehydrocoupling of B—H and N—H bonds, and (b) pyrolyzing the reaction product of step (a).

MODES FOR CARRYING OUT THE INVENTION

While the invention is particularly exemplified herein with respect to making BN precursors from B—H bond-containing and N—H bond-containing reactants, the invention process is generally applicable to making compounds of B and other Group VA nonmetals (P, As, Sb, and Bi) and compounds of other Group IIIA metals (Al, Ga, In, Tl) and nitrogen or another Group VA nonmetal. Thus, the process may be used to make precursors to compounds such as BP, BAs, BSb, AlN, AlP, AlAs, GaAs, GaN, GaP, InN, InP, and InAs. Accordingly, in the following discussion other Group IIIA metals may be substituted for boron and other Group VA nonmetals for nitrogen as the case may be, to provide suitable reactants for making such precursors. For the purpose of this invention, Group IIIA metals of atomic number 5 to 49, inclusive and Group VA nonmetals of atomic number 7 to 33, inclusive are preferred.

Catalysts suitable for carrying out the reaction between the M—H and Z—H bond-containing reactants are metal complexes such as those indicated in Table I below which are homogeneous catalysts that dissolve in the reactants or in a solvent used to dissolve the reactants. Heterogeneous catalysts such as those of Table II may also be used or mixtures of homogeneous catalysts and/or heterogeneous catalysts. In general, catalysts that activate the dehydrocoupling of the M—H bond and the Z—H bond may be used. Also, mixtures of catalysts may be used. The catalyst may be supported on a polymer, inorganic salt, carbon, or ceramic material. The heterogeneous catalyst may be provided in a designed shape, such as particles porous plates and the like.

TABLE I $H_4Ru_4(CO)_{12}$, $Ru_3(CO)_{12}$, $Fe_3(CO)_{12}$,
$Rh_6(cO)_{16}$, $Co_2(CO)_8$ $(Ph_3P)_2Rh(CO)H$,
$H_2PtCl_6$, nickel cyclooctadiene,
$Os_3(CO)_{12}$, $Ir_4(CO)_{12}$, $PdCl_2$,
$(PhCN)_2PdCl_2$, $(Ph_3P)_2Ir(CO)H$,
$Pd(OAc)_2$, $Cp_2TiCl_2$, $(Ph_3P)_3RhCl$,
$H_2Os_3(CO)_{10}$, $Pd(Ph_3P)_4$,
$Fe_3(CO)_{12}/Ru_3(CO)_{12}$, complexes of metal hydrides.

Ph = phenyl;
Ac = acetyl;
Cp = cyclopentadienyl

TABLE II

Alkaline metals (e.g., Na, K), Pt/C, Pt/Cl, Pt/BaSO$_4$,
Cr, Pd/C, Co/C, Pt black, Co black, Pd black,
Ir/Al$_2$O$_3$,Pt/SiO$_2$, Rh/TiO$_2$,
Rh/La$_2$O$_3$, Pd/Ag alloy, LaNi$_5$, PtO$_2$,
transition metal salts, transition metal
hydrides or other transition metal oxides.

In the case of nitride precursors, the reactant that provides the N—H bond may be ammonia, a primary amine or a secondary amine (hydrazines and polyamines being within the scope of the term "amine"). These amines may be represented by the general formula:

$(R)_2NH$ where the radicals represented by R are the same or different and may be combined to form a cyclic structure with the nitrogen atom of the amine. R will commonly represent hydrogen or a hydrocarbyl radical such as lower ($C_1$ to $C_4$) alkyl, alkenyl, alkynyl, phenyl and lower alkyl-substituted phenyl, fused ring aromatic, usually of 8 to 20 carbon atoms or cycloaliphatic of 6 to 8 annular carbon atoms, such as cyclohexyl. Alkyl radicals greater than $C_4$ may be used but the resulting products are typically not useful as ceramic precursors. Such hydrocarbyl groups may be substituted with amino, hydroxyl, ether, ester, or other nonhydrocarbyl moieties. In the case of hydrazines R contains at least one nitrogen atom and the reactant contains an N—N bond. R may also represent an amine, an alkoxide of 1 to 10 carbon atoms, or an organometallic radical such as silyl or boryl. Salts of such N—H containing compounds may be used such as hydrohalide salts.

Preferred N—H group-containing reactants for making preceramic materials are ammonia, primary amines, hydrazines and polyamines of the above formula an organometallic amine, amine borane complexes and borazine.

Phosphines or arsines corresponding to the above amines may be used when the Group VA nonmetal is P or As, respectively.

The M—H group-containing reactant may be a hydride, an organohydride, a complex of a hydride, e.g., hydride-amine complexes such as amine borane complex, borazine or borazole carborane, diborane, polyaminoboranes, a borane salt, a borane cluster or such analogs with other Group IIIA metals. Exemplary hydrides are boron hydride (borane), aluminum hydride, and gallium hydride. The hydrides and organohydrides may be represented by the formula:

$(R_2)MH$ where R is generally as defined above. Salts of these hydrides may be used.

The reaction is carried out in solution with the solvent being the reactants themselves or an added non-reactive organic solvent such as a hydrocarbon, an ether (e.g. ethyl ether, tetrahydrofuran), a halogenated hydrocarbon ($CHCl_3$, $CH_2Cl_2$, $ClCHF_2$, $ClCH_2CH_2Cl$) an aromatic such as benzene, toluene or methylphenyl ether or a polar solvent such as acetonitrile, dimethylformamide, pyridine, or a tertiary amine. Mild temperatures that activate the catalyst are used. Such temperatures will normally be in the range of $-20°$ C. to $250°$ C. Some reactions may be carried out in the gas phase by flowing M—H and Z—H components over a metal catalyst. Such reaction may be useful especially for CVD techniques. If desired, the activation of the catalyst by heating may be supplemented with activation by treatment of the reaction medium with particulate or nonparticulate radiation. It may also be activated by promoters such as acids bases oxidants, hydrogen or may be stabilized by reagents such as amines, phosphines, arsines and carbonyl. The mol ratio (Z—H:-M—H) of the reactants will normally be in the range of 3:1 to 1:3, with stoichiometric, proportions being preferred. An excess of either reactant outside of this range may be used, if desired, for kinetic or thermodynamic control. The concentration of catalyst will usually be less than or equal to about 5 mol percent based on the total moles of reactants usually 0.1 to 5 mol percent. When one of the reactants is gaseous (e.g. when ammonia is used to provide the N—H bond). Pressure and higher ratios of gaseous to liquid or solid reactant may be used to control the concentration of the gaseous reactant in the reaction medium.

The mol ratio of M to Z in the product of the reaction will usually be in the range of 1:3 to 3:1.

Monomers, oligomers, or polymers containing M—Z bonds produced by the above described process may be cleaved in the presence of the metal catalyst with or without hydrogen or a hydrogen donor and the cleavage product further reacted to provide oligomers or polymers containing a multiplicity of M—Z bonds or compounds containing a new M—Z bond. This reaction may involve opening a ring at an M—Z bond or cleaving an open chain at an M—Z bond. The resulting fragment or fragments may react with one another (to form oligomers or polymers) or with added Z—H-containing reactants such as ammonia or amines, and/or added M—H-containing reactants to form new M—Z bonds. It is thus apparent that reaction of the M—H and Z—H compounds or cleavage of an M—Z bond-containing compound may be succeeded by subsequent reactions of either of such types of reaction or a mixture of both.

The precursors made according to the invention may be pyrolyzed as is known in the art to provide ceramics. Suitable combinations of metal and nonmetal (e.g. Ga and As) may provide materials with useful electronic properties.

The following examples further illustrate, the process of this invention. These examples are not intended to limit the invention in any manner.

EXAMPLES

General Procedure

All reactions were run in stainless steel Parr reactors equipped with pressure gauges to follow gas evolution. The evolved gases were released periodically and the reactors were recharged with amine or ammonia gas as necessary. The inlet pressure provided in the examples are the sum of several partial pressures charged into the reactors. After each charge, much of the pressure was lost through dissolution of the gas into the reaction solvent. Blank reactions (without catalyst) provide the necessary contrast.

Bulk pyrolysis reactions were performed under flowing nitrogen (1 atm). The pyrolysis schedule used was a continuous temperature range at 0.5° C./min from room temperature to 850° C. and a 3 hour hold at this elevated temperature.

Abreviations used in the examples are Me=methyl, Pr=propyl, THF=tetrahydrofuran NMR=nuclear magnetic resonance. IR=infrared GC=gas chromatography and MS=mass spectrometry.

1. Reaction of $BH_3.NMe_3$ with propylamine

A solution containing 3.0 g (41 mmol) borane-trimethylamine complex, 4.85 g (82 mmol) propylamine and 32 mg (0.050 mmol) $Ru_3(CO)_{12}$ in 15 ml benzene was heated at 60° C. Pressure was released every 2–3 hours. After 32 hours the total gas pressure formed summed to 2020 psi (~61 mmol) and no further evolution was observed. Benzene was evaporated by purging nitrogen through the solution and 4.5 g of products were obtained (88% yield based on initial quantities of borane and propylamine). Only 160 psi of pressure released in the uncatalyzed reaction and product yield was 3.6 g with $BH_3.NMe_3$ and $BH_3.HN_2Pr$ being the majority of the product. H-NMR of the catalyzed reaction showed the complete disappearance of trimethylamine (2.62 ppm) and the presence of several different propylamine (C—H) groups. The triplet signal of the α amino hydrogens (2.65 ppm) was converted into a major quartet (probably two overlapped triplets) centered at 2.73 ppm (J-8H$_z$) and a minor multiple centered at 3.07 ppm which may indicate amine bonded to two boron atoms. Analogous spectra of the blank reaction provides evidence for the presence of $BH_3.NMe_3$ and $BH_3.H_2NPr$ complexes together with other aminoborane products with a ratio of approximately 1.0:2.5:1.1 respectively based on the integration of the α amino hydrogen. GC-MS spectra of this reaction showed the two complexes together with $(PrNH)_2BH$. These products were absent in the catalyzed reaction which contains tri-N-propylborazine as the major volatile product detected by GC-MS.

IR spectra are additional support to the above observations. The catalyzed reaction products showed IR absorptions for N—H (3463 cm$^{-1}$) and B—H (2492 cm$^{-1}$) bands together with very strong broad stretches in the borazine region (1500–1400 cm$^{-1}$). The blank spectrum included several N—H and B—H bands that match patterns known for borane-amine complexes.

Details of these analyses are given below.

| | Catalyzed Reaction | Blank Reaction | $BH_3.NMe_3$ |
|---|---|---|---|
| | $^1$H NMR (CDCl$_3$, Ref CHCl$_3$, δ, ppm) | | |
| | 3.07 (m, 0.8H) | 2.69 (m, 6H) | |
| | 2.73 (q, 1.2H) | 2.62 (Δ, 3H) | |
| | | 2.21 (Δ, 1.4H) | |
| | 1.42 (m, 2H) | 1.43 (m, 2H) | |
| | 0.89 (dt, 3H) | 0.89 (t, 3H) | |
| | IR (CCl$_4$, cm$^{-1}$) | | |
| N—H | 3460 (m, sharp) | 3318 (m) | |
| | | 3238 (s, bm) | |
| | | 3155 (m) | |
| C—H | 2968 (vs) | 3020 High | 3025 (m) 2925 (sh) |
| | 2939 (vs) | 2968 (s) | 3005 (s) |
| | 2882 (vs) | 2939 (s) | 2985 (m) |
| | | 2880 (m) | 2943 (s) |
| B—H | 2492 (m) | 2370 (vs) | 2380 (vs) |
| | | 2322 (vs) | 2328 (vs) |
| | | 2272 (vs) | 2278 (vs) |
| NH$_2$ | 1610 (w) | | |
| B—N | 1500 (vs, br) | 1600 (s) | 1550 (m) |
| C—C | 1470 (vs, br) | 1482 (m) | 1487 (vs) |
| | 1440 (sh) | 1460 (s) | 1466 (vs) |
| | 1387 (m) | 1385 (w) | 1410 (m) |
| | 1370 (w) | 1317 (w, br) | |
| | 1365 (w) | | |
| | 1348 (w) | | |
| C—N | 1310 (m) | 1295 (w) | 1262 (s) |
| | 1290 (m) | 1248 (m) | 1262 (vs) |
| | 1260 (sh) | 1210 (w) | 1170 (vs) |
| | 1248 (w) | 1170 (s) | 1122 (s) |
| | 1200 (vw) | 1118 (m) | |
| | 1149 (m) | 1055 (w) | |
| | 1072 (m) | | |

Fractional distillation (100° C./170μ) of the catalyzed reaction yielded 80% of volatile products identified by GC-MS.

Tri-N-propylborazine was the major product (57%: 39° C./170μ). All other products were collected fractionally as mixtures at 77°–100° C./170μ.

$^1$H-NMR spectrum of tri-N-propylborazine showed a quartet at 2.73 ppm for the α amino hydrogen which should be the superposition of two different triplets, together with two sets of almost overlapped multiplet at 1.42 ppm and a triplet at 0.91 ppm. It is suggested that the tri-N-propylborazine is a cis, trans, trans product.

2. Reaction of borane-ammonia complex ($BHS_3.NH_3$)

A solution of 1.0 g (32 mmol) $BH_3.NH_3$ and 32 mg (0.05 mmol) $Ru_3(CO)_{12}$ in 15 ml benzene was heated at 60° C. under $N_2$ for 85 hours (the complex does not dissolve completely).

Pressure was released after 21 hours (210 psi) and 65 hours (310 psi). A total of 610 psi of gas was released over the reaction period. An insoluble solid product was obtained after solvent evaporation. The blank reaction released only 70 psi of gas after 85 hours of heating. The elemental analysis for the catalyzed reaction products showed the following elemental analysis.

| Elemental Analysis | B | N | H |
|---|---|---|---|
| $BH_3.NH_3$ | 35.48 | 45.16 | 19.35 |
| Catalyzed reaction | 30.87 | 45.02 | 13.57 |
| Blank reaction | 33.42 | 44.69 | 16.36 |

This elemental analysis reveals compositional differences between the products of the catalyzed and uncatalyzed reactions. These differences show up in the yields of ceramic products. Ceramic yield for the catalytic reaction was 68% while the yield for the uncatalyzed reaction was 64%.

3. Reaction of Borane-trimethylamine Complex (BH₃.NMe₃) with Ammonia

To a solution of 3.0 g (41 mmol) borane-trimethylamine and 32 mg 10.05 mmol) $Ru_3(CO)_{12}$ in 15 ml benzene were charged 250 psi ammonia. The reaction was carried on at 60° C. for 36 hours. Gas evolution resulted in pressure buildup. At pressures of approximately 250 psi gas was released and the reactor was recharged with ammonia. Approximately 1200 psi (~61 mmol) of ammonia were added over the period of reaction and 1570 psi (~95 mmol) of gases ($H_2$, $NH_3$ and $Me_3N$) were released. A suspension of 0.63 g white fine powder was obtained in an orange-brown solution. The analysis of GC and ¹H-NMR revealed the presence of starting material as well as other unidentifiable products. A ceramic yield of 73% was obtained upon pyrolysis of the insoluble powder. The blank reaction solution stayed homogeneous and the solid that remained after removal of solvent appeared to be mainly $BH_3.NMe_3$ which gives a 2% ceramic yield when pyrolyzed. The elemental analysis of the powder showed that it contains 7.99% carbon which is related to the remains of $BH_3.NMe_3$ and indicates that it is present as approximately 6% of the solid material. The rest of the powder may have the following structure:

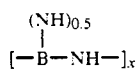

The analysis of the pyrolyzed material showed oxygen contamination with very small amount of ceramic carbon. Following recalculation in which each oxygen is counted as $(NH)_{0.5}$, it is clear that there is incomplete conversion to BN at 900° C.

| | \multicolumn{5}{c}{Elemental Analysis} |
|---|---|---|---|---|---|
| | B | N | C | H | O | TOTAL |
| Precursor powder | 29.43 | 56.09 | 7.99 | 6.42 | — | 99.97 |
| Pyrolyzed powder | 32.07 | 49.72 | 2.72 | 0.89 | 0.10 | 88.02 |

4. Reaction of BH₃.NMe₃ with methylamine

To a solution of 5.0 g (68 mmole) $BH_3.NMe_3$ and 32 mg (0.05 mmol) $Ru_3(CO)_{12}$ in 15 ml benzene were added approximately 150 psi (~9 mmol) methylamine. The solution was heated at 60° C. for 9.5 hours until no additional pressure was evolved. The pressure was released every 1-2 hours and the reaction was recharged with methylamine. The total pressure of added amine was 1200 psi (~73 mmol) and the total evolved was 2220 psi (136 mmol). A mixture of oily products (2.0 g, 46% yield based on boron) was obtained after solvent evaporation by nitrogen purging through the solution. This mixture became viscous upon sitting for 2 weeks at room temperature under $N_2$. GC-MS analysis revealed tris-B-methylamine-tri-N-methylborazine-[MeHNB-NMe]₃— (M.W.=210), as the major volatile product together with small amounts of trismonomethylborane, $B(NHMe)_3$, and mono- and di-substituted B-methylaminoborazines. H-NMR indicated the disappearance of borane-trimethylamine complex ($\delta$=2.62 ppm) and the presence of different types of $CH_3$—N groups. IR spectrum includes N—H bands, a variety of different B—H bands, and borazine B—N stretches around 1500, 1450, and 1400 cm⁻¹. Side chain B—N band absorption appears near 1360 cm⁻¹.

No pressure or product formation (beside the methylamine-borane complex) is observed in the blank rection. The elemental analysis, given below, corrected for some oxygen contamination gives the following molecular structure:

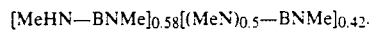

Therefore the proposed polymeric structure is that of PBZ given above where the average degree of polymerization, x, is 3.

| Elemental Analysis | B | N | C | N | O |
|---|---|---|---|---|---|
| product (found) | 17.37 | 37.79 | 21.12 | 9.33 | 1.98 |
| product, corrected for oxygen | 17.32 | 39.47 | 33.83 | 9.37 | — |
| proposed structure (calc. for x = 3) | 17.42 | 39.43 | 33.80 | 9.35 | — |

A ceramic yield of 60% is obtained upon pyrolysis. The ceramic material elemental analyses, given below for pyrolysis at 850° C. and 1600° C., reveals the presence of high carbon content (24.52%, 15.42%) as expected for such high ceramic yield. It also shows a nitrogen to boron mol ratio of 1.26:1.00 (at 850° C.) as well as the presence of hydrogen and oxygen. However, according to mass calculation only 17% (at 850° C.) of the boron content of the preceramic material is missing due to fragmentation upon pyrolysis.

| | \multicolumn{6}{c}{Elemental analysis of pyrolyzed material} |
|---|---|---|---|---|---|---|
| | Temp °C. | B | N | C | H | O |
| percent (%) | 850 | 23.97 | 38.44 | 24.52 | 1.08 | 4.80 |
| mol ratio | | 1.00 | 1.26 | 0.93 | 0.50 | 0.13 |
| percent (%) | 1600 | 36.71 | 42.48 | 15.42 | 1.45 | 2.05 |
| mol ratio | | 1.00 | 0.91 | 0.38 | 0.50 | 0.13 |

X-ray powder diffraction analysis shows no crystalinity pattern after pyrolysis. Further heating to 1600° C. in attempt to obtain an identifiable x-ray powder diffraction pattern decreases the total yield based on the preceramic polymer to 49% (pyrolysis yields at the different temperatures used are shown below). Yet no such pattern is observed. The absence of BN, $B_4C$ and C crystalites indicates the possibility that a new composition of matter has been formed.

| \multicolumn{3}{c}{Pyrolysis yield results based on the preceramic polymer} |
|---|---|---|
| Temperature Range (°C.) | Theoretical for BN (%) | Found (%) |
| 25-850 | 40 | 60 |
| 850-1600 | 62 | 81 |
| 25-1600 (total) | 40 | 49 |

5. Reaction of BH₃.THF₂ with methylamine

To a solution of 5 ml borane in THF (1M; 5 mmol) are added 32 mg $Ru_3(CO)_{12}$. The reactor is charged with 50 psi (~5 mmol) methylamine and heated at 90°

C. for 5 hours. GC-MS analysis suggests the formation of 3 products: B(NHMe)$_3$ (M.W. 101, major);

MeNHB-O-C$_4$H$_9$ cyclic (M.W. 113, minor); (MeNH)$_2$BOC$_4$H$_9$ (M.W. 144, minor). No reaction was observed in the absence of catalysts.

6. Reaction of BH$_3$.NMe$_3$ with dimethylamine

To a solution of 3.0 g (41 mmol) of borane-trimethylamine complex and 32 mg (0.05 mmol) Ru$_3$(CO)$_{12}$ in 15 ml benzene were charged approximately 100 psi of dimethylamine. The solution was heated at 60° C. and pressure was released every 3.5 hours followed by recharging with dimethylamine. After 51 hours no more gases were evolved (1800 psi). The solvent was evaporated by nitrogen purging to yield 0.8 g of solid material. GC analysis indicated only small amounts of (Me$_2$N)$_3$B (compared with commercial sample).

$^1$H-NMR of the benzene solution indicates different CH$_3$—N groups with the following integration ratios. 2.72 (1.00). 2.53 (0.17, Me$_2$N)$_3$B), 2.41 (0.22), 2.20 (0.07).

IR stretches at 2485(s), 2447(s), 2385(m), 2322(W), 2280(sh), 2215(W) suggests B—H bands of borane-amine compounds beside a small amount of borane-amine complexes.

The above data point to the formation of volatile products. Probably mono- and bis-dimethylaminoborane, beside a small amount of tris-dimethylaminoborane and borane-dimethylamine complex.

7. Reaction of BH$_3$.NH$_3$ with [H$_2$SiNMe]$_x$ (x=19)

A solution of 2.0 g (33.9 mmol) [H$_2$SiNMe]$_x$, 0.25 g (8.1 mmol) BH$_3$.NH$_3$ and 16 mg Ru$_3$(CO)$_{12}$ in 2 ml of benzene is heated at 70° C. The borane-ammonia complex does not dissolve completely in the solution prior to heating. After 3 hours of heating, pressure above the reaction is 70 psi.

Heating is continued for an additional 4 hours. No pressure evolution is observed in the blank reaction. Homogeneous mixed rubbery products are formed in both the catalyzed and uncatalyzed reactions.

| Elemental Analysis | Si | B | N | C | H | O |
|---|---|---|---|---|---|---|
| Reactants (calc.) | 42.16 | 3.96 | 26.11 | 18.07 | 9.69 | — |
| Catalyzed | 40.21 | 4.75 | 20.77 | 15.03 | 6.80 | 0.59 |
| Blank | 45.03 | 2.39 | 22.13 | 15.68 | 7.17 | 0.69 |

8. Reaction of BH$_3$.NMe$_3$ with [H$_2$SiNMe]$_x$

To a solution of 1.0 g (34 mmol) [H$_2$SiNMe]$_{19}$, 0.62 g (8.5 mmol) BH$_3$.NMe$_3$ and 16 mg (0.025 mmol) Ru$_3$(CO)$_{12}$ in 15 ml of benzene are charged 60 psi of methylamine. One-hundred twenty psi of pressure are formed and released after 1.5 hours, then reheated for an additional 1.5 hours.

An oily liquid remains after solvent evaporation (2.4 g, 90%) which becomes a rubber after several days at room temperature under N$_2$. Pressure evolution is not observed in the blank reaction and heterogeneous mixture of liquid containing precipitate is obtained after the solvent removal. Ceramic yields of 52% and 51%, respectively, remain after pyrolysis.

Modifications of the above described modes for carrying out the invention that are obvious to persons of skill in the field of organometallic chemistry are intended to be within the scope of the following claims.

We claim:
1. A process for making a ceramic product, comprising the steps of:
    (a) reacting a first reactant that has at least one Z—H bond, where Z represents a Group VA nonmetal, with a second reactant that has at least one M—H bond, where M is a Group IIIA metal, in the presence of a metal catalyst that catalyzes dehydrocoupling of the Z—H and M—H bonds, at a reaction temperature in the range of −20° C. and 250° C., to give a preceramic compound containing at lease one Group IIIA metal-Group VA nonmetal bond; and
    (b) pyrolyzing the preceramic compound to give said ceramic product.
2. The process of claim 1, wherein M represents a Group IIIA metal having an atomic number of 5 to 49, inclusive.
3. The process of claim 1, wherein Z represents a Group VA nonmetal having an atomic number of 7 to 33, inclusive.
4. The process of claim 2, wherein Z represents a Group VA nonmetal having an atomic number of 17 to 33, inclusive.
5. The process of claim 1, wherein Z represents nitrogen.
6. The process of claim 1, wherein M represents boron.
7. The process of claim 5, wherein M represents boron.
8. The process of claim 1, wherein the second reactant is an amine borane complex selected from the group consisting of BH$_3$.NH$_3$ and BH$_3$.NMe$_3$, where Me represents methyl.
9. The process of claim 1, wherein the first reactant is methylamine.
10. The process of claim 8, wherein the first reactant is methylamine.
11. The process of claim 1, wherein the first reactant is a polysilazane.
12. The process of claim 8, wherein the first reactant is a polysilazane.
13. The process of claim 11, wherein the polysilazane is of the formula

(H$_2$SiNMe)$_x$ where Me represents methyl and x is an integer greater than 4.
14. The process of claim 12, wherein the polysilazane is of the formula (H$_2$SiNMe)$_x$ where Me represents methyl and x is an integer greater than 4.
15. The process of claim 1, wherein the ceramic product is prepared as a coating.
16. The process of claim 1, wherein the ceramic product is prepared as a fiber.
17. The process of claim 1, wherein the ceramic product is prepared as a shaped product.

18. A process for preparing a shaped ceramic product, comprising the steps of:
(a) reacting a first reactant that has at least one Z—H bond, where Z represents a Group VA nonmetal, with a second reactant that has at least one M—H bond, where M is a Group IIIA metal, in the presence of a metal catalyst that catalyzes dehydrocoupling of the Z—H and M—H bonds, at a reaction temperature in the range of −20° C. and 250° C., to give a tractable, nonvolatile preceramic compound containing at least one group IIIA metal-Group VA nonmetal bond;
(b) shaping said preceramic compound to give a desired form; and
(c) pyrolyzing said shaped preceramic compound to give a ceramic product in shaped form.

19. The process of claim 18, wherein said shaped form is a fiber.